(12) United States Patent
Lee

(10) Patent No.: US 6,386,876 B1
(45) Date of Patent: May 14, 2002

(54) UNIVERSAL TISSUE EMERGENCE PROFILE SHAPING HEALING ABUTMENT, PROVISIONAL AND RESTORATION ABUTMENTS, IMPRESSION COPING AND CERAMIC CROWN BASE SYSTEM

(76) Inventor: Kenneth K. S. Lee, 210 - 2425 Oak Street, Vancouver (CA), V6H 3S7

(*) Notice: Subject to any disclaimer, the term of this patent is extended or adjusted under 35 U.S.C. 154(b) by 0 days.

(21) Appl. No.: 09/725,205

(22) Filed: Nov. 29, 2000

(51) Int. Cl.$^7$ .................................................. A61C 8/00
(52) U.S. Cl. ....................................................... 433/173
(58) Field of Search ................................ 433/172, 173, 433/174, 175, 176

(56) References Cited

U.S. PATENT DOCUMENTS

| | | |
|---|---|---|
| 4,330,891 A | 5/1982 | Branemark et al. |
| 4,960,381 A | 10/1990 | Niznick ....................... 433/174 |
| 5,030,095 A | 7/1991 | Niznick ....................... 433/173 |
| 5,062,800 A | 11/1991 | Niznick ....................... 433/229 |
| 5,316,477 A * | 5/1994 | Calderon ..................... 433/173 |
| 5,334,024 A | 8/1994 | Niznick ....................... 433/173 |
| 5,433,606 A | 7/1995 | Niznick et al. .............. 433/174 |
| 5,571,017 A | 11/1996 | Niznick ....................... 433/173 |
| 5,575,650 A | 11/1996 | Niznick et al. |
| 5,582,299 A | 12/1996 | Lazzara et al. ............. 206/63.5 |
| 5,603,338 A | 2/1997 | Beaty .......................... 128/898 |
| 5,622,500 A | 4/1997 | Niznick ....................... 433/173 |
| 5,662,473 A * | 9/1997 | Rassoli et al. .............. 433/172 |
| 5,759,036 A * | 6/1998 | Hinds .......................... 433/173 |
| 5,879,161 A * | 3/1999 | Lazzara ....................... 433/173 |
| 6,039,568 A * | 3/2000 | Hinds .......................... 433/173 |

* cited by examiner

Primary Examiner—Cary E. O'Connor
(74) Attorney, Agent, or Firm—Oyen Wiggs Green & Mutala

(57) ABSTRACT

This invention relates to a novel, universal tissue emergence profile shaping healing abutment, provisional and restoration abutments, impression coping and ceramic crown base system. More particularly, this invention pertains to a novel dental implant system which provides a simple related series of an emergent profile healing abutment, which can be custom shaped to a specific tooth socket, an impression coping provisional and final restoration abutment system, and a ceramic base on which to build a crown. A dental abutment for use in association with a dental implant comprising: (a) a non-cylindrical gingival tissue abutment with an implant bearing surface on a first side thereof, a passage through the abutment and the bearing surface for receiving a screw to enable the bearing surface of the abutment to be secured to the dental implant; and (b) a hollow protrusion surrounding the passage and located on a second side of the abutment.

15 Claims, 7 Drawing Sheets

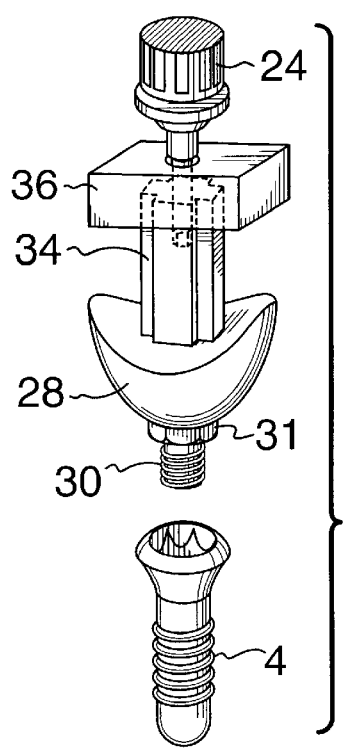
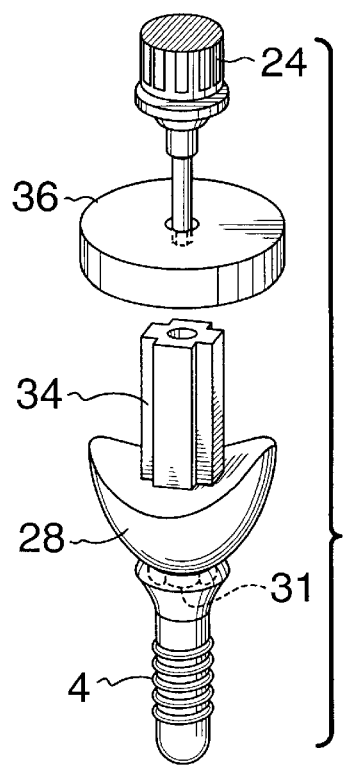
FIG. 10
FIG. 11
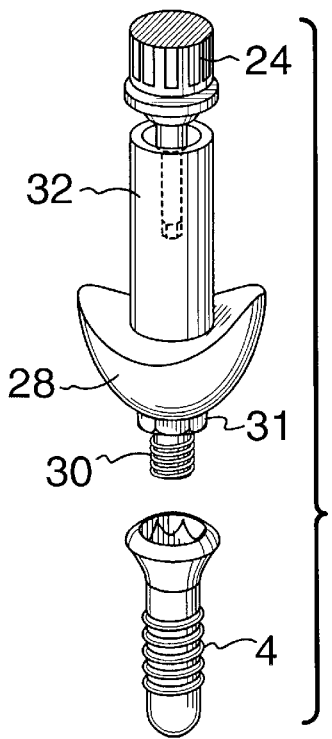
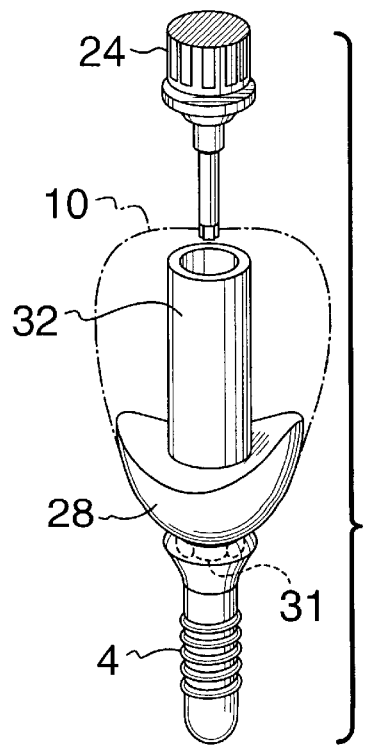
FIG. 12
FIG. 13

US 6,386,876 B1

UNIVERSAL TISSUE EMERGENCE PROFILE SHAPING HEALING ABUTMENT, PROVISIONAL AND RESTORATION ABUTMENTS, IMPRESSION COPING AND CERAMIC CROWN BASE SYSTEM

FIELD OF THE INVENTION

This invention relates to a novel, universal tissue emergence profile shaping healing abutment, provisional and restoration abutments, impression coping and ceramic crown base system. More particularly, this invention pertains to a novel dental implant system which provides a simple related series of an emergent profile healing abutment, which can be custom shaped to a specific tooth socket, an impression coping provisional and final restoration abutment system, and a ceramic base on which to build a crown.

BACKGROUND

The technology of dental implants has been evolving over the years with both advances and setbacks. One implant system, known as the Branemark system for permanent tooth replacement has been supplied by Noblepharma, AB, Sweden, for over thirty years. U.S. Pat. No. 4,330,891 pertains to this system.

More than twenty years ago, a dental implant concept to prevent tissue destruction after tooth extraction was developed by a research team headed by Dr. Wylli Schulte. Dr. Wylli Schulte and his team did their development work at The Universities of Tubingen and Heidelberg. The system became known as the Tubingen implant. Dr. Schulte developed a ceramic stepped implant prosthetic which mimicked the tooth root and fit in the bone socket from which the root had been extracted.

Subsequently, the stepped ceramic implant was replaced by a titanium implant which had a stepped cylindrical design analogous to the tooth root at both the cervical and apical ends. This concept of diameter-guided implant planning provides a number of important advantages. It provided support of the alveolar bone from the root analog shape of the implants. It also provided a minimal loading of the peri-implant bone under the impact of chewing forces and minimized perforation risk of the vestibular lamella or injury of adjacent teeth during preparation of the implant site. The titanium implant system is sold by Friatec Dental Inc. under the trademark FRIALIT-2.

Other implant systems are manufactured by other companies, and without being exhaustive, titanium implant systems are available from Institut Straumann AG, Switzerland, under the trademark ITI, 3i Corporation, Palm Beach Gardens, Fla., under the trademark TG OSSEOTITE, protected by U.S. Pat. Nos. 5,603,338 and 5,582,299, and Paragon Implant Company, Etobicoke, Ontario M9W 5Z5.

Institut Straumann AG utilizes an implant system which was pioneered by Dr. Andre Schroeder. Straumann has over the years developed and marketed a successful and improved titanium implant system under the trademark OCTASYSTEM. The implant uses an octagonal implant/abutment and Moore taper interface which provides great longlasting tooth stability.

Paragon Implant Company has obtained a number of U.S. patents, G. A. Niznick, which protect friction fit, internal hex and taper lock, external hex implant systems designed to eliminate or minimize rotational wobble in screw-retained abutments. These systems are designed to reduce rotational misfit with different non-rotating implant interfaces.

Specifically, U.S. Pat. No. 5,030,095 protects a twenty-four position pre-angled abutment design. U.S. Pat. No. 5,062,800 protects a fixture mount packaging system. U.S. Pat. No. 5,334,024 protects a friction-fit abutment system. U.S. Pat. No. 4,960,381 protects an internal hex-thread connection. U.S. Pat. No. 5,575,650 protects a twist trispade drill with counter sink system. U.S. Pat. No. 5,622,500 protects a healing collar packaging. U.S. Pat. No. 5,571,017 protects a selective surface for an implant. U.S. Pat. No. 5,433,606 protects a tapered external hex connection between abutment and implant.

SUMMARY OF INVENTION

The invention is directed to a dental abutment for use in association with a dental implant comprising: (a) a non-cylindrical gingival tissue abutment with an implant bearing surface on a first side thereof, a passage through the abutment and the bearing surface for receiving a screw to enable the bearing surface of the abutment to be secured to the dental implant; and (b) a hollow protrusion surrounding the passage and located on a second side of the abutment.

The protrusion can be a hollow tube which can be in axial alignment with the passage and the implant. The abutment can include a screw which can fit within the passage and connect the abutment with the implant. The bearing surface can have an octagonal base for use in association with an octagonal recess implant.

The abutment can be formed of a dentally acceptable machinable material, the outer surface of which can be shaped by an implantologist to fit within a cavity of gingival tissue formed by extraction of a tooth.

The abutment can have an ovoid shape, a tapered conical oval cross-section shape, a tapered truncated shape with a triangular cross-section or a tapered truncated shape with a rectangular cross-section.

The abutment can include an impression coping and an associated seating cap. The seating cap can be cylindrical or cuboidal in shape.

The protrusion can be a plastic tube which can be used for wax pattern burnout in forming a crown.

The abutment can include a temporary crown or a permanent crown associated with the abutment. The abutment can include a base for a ceramic crown restoration.

BRIEF DESCRIPTION OF DRAWINGS

In drawings which illustrate specific embodiments of the invention, but which should not be construed as restricting the spirit or scope of the invention in any way:

FIG. 10 illustrates an exploded perspective view of an emergence profile impression coping with screw and plastic seating cap, for use in association with the OCTASYSTEM implant.

FIG. 11 illustrates a perspective view of the emergence profile impression coping and seating cap installed onto the OCTASYSTEM implant.

FIG. 12 illustrates an exploded perspective view of an emergence profile provisional or final restoration abutment with screw and plastic tube, used for providing a wax pattern for burnout and crown manufacture, in association with an OCTASYSTEM.

FIG. 13 illustrates a perspective view of the emergence profile provisional or final restoration or ceramic base abutment, according to the invention, installed onto the OCTASYSTEM implant with a plastic tube used for wax pattern burnout. The artificial tooth is illustrated in dotted lines.

DETAILED DESCRIPTION OF SPECIFIC EMBODIMENTS OF THE INVENTION

Figure 1:
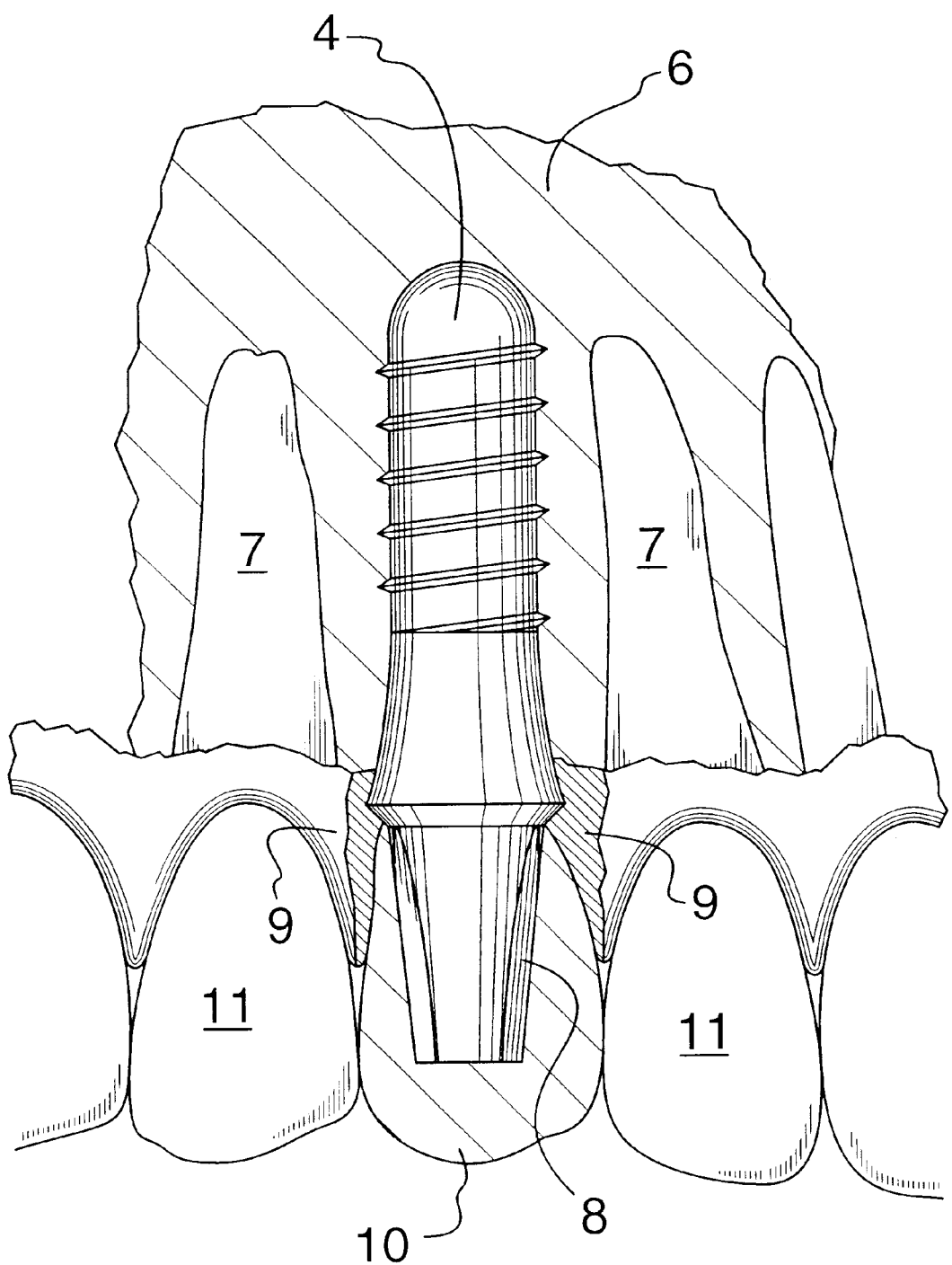
FIG. 1 illustrates a stylized perspective view of a typical titanium dental implant system manufactured by Institut Straumann AG and sold under the trademark OCTASYSTEM.

FIG. 1 illustrates a stylized perspective view of a typical titanium dental implant system manufactured by Institut Straumann AG and sold under the trademark OCTASYSTEM. As readily visible in FIG. 1, the OCTASYSTEM implant 4 is shown installed in jawbone 6 with abutment 8 secured to the implant 4, and an artificial tooth 10 built onto the abutment 8. The implant 4, abutment 8 and artificial tooth 10 are installed between a pair of normal teeth 11 secured by respective roots 7 in the jawbone 6.

Figure 2:
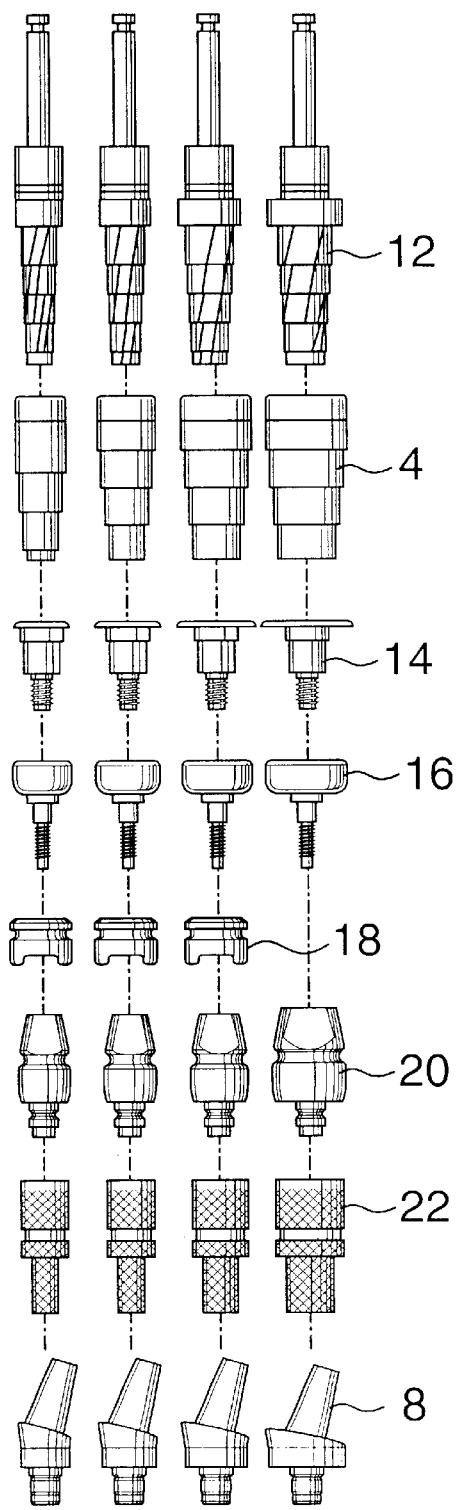
FIG. 2 illustrates for comparison purposes a series of dental implant tools and components as manufactured by Friatec Dental Inc. and sold under the trademark FRIALIT-2.

FIG. 2 illustrates for background prior art purposes a series of dental implant tools and components as manufactured by Friatec Dental Inc. and sold under the trademark FRIALIT-2. As illustrated in FIG. 2, Friatec Dental Inc. provides a series of four sizes of drills 12, implants 4, sealing screws 14, gingiva former 16, impression coping seating caps 18, impression coping 20, implant analogs 22 and abutments 8.

Figure 3:
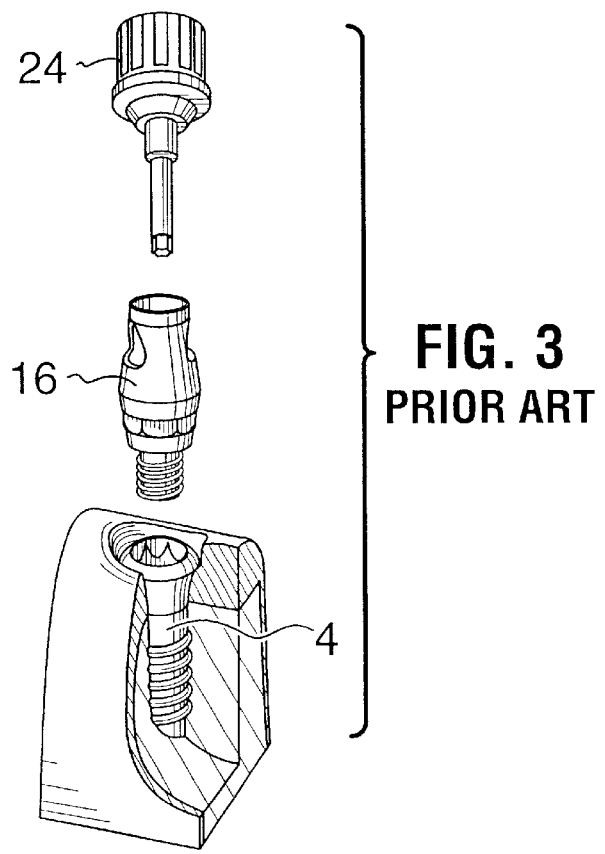
FIG. 3 illustrates a schematic exploded perspective view of an Institut Straumann AG OCTASYSTEM implant installed in stylized representation of a jaw bone, with an abutment being installed by a screwdriver, as manufactured and sold by Institut Straumann AG.

FIG. 3 illustrates a schematic exploded perspective view of an Institut Straumann AG OCTASYSTEM implant installed in stylized representation of a jaw bone, with an abutment being installed by a screwdriver. Specifically, FIG. 3 illustrates in exploded stylized manner, the installation of an OCTASYSTEM implant 4 with abutment 16 ready for installation in the implant 4 by means of OCTASYSTEM screwdriver 24.

Figure 4:
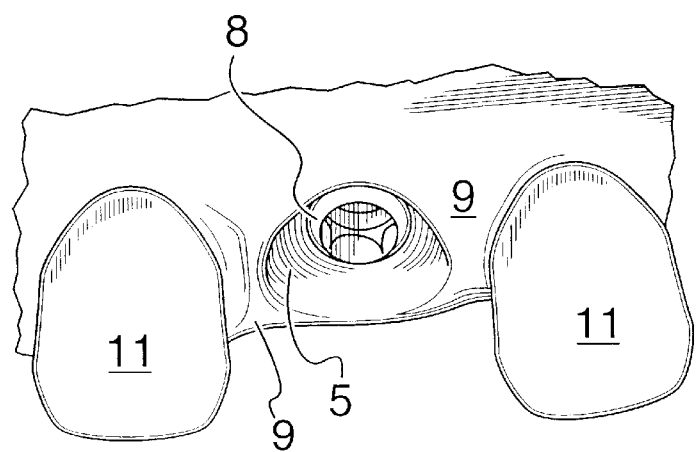
FIG. 4 illustrates a perspective view of an Institut Straumann AG OCTASYSTEM implant installed in a root cavity between a pair of normal teeth.

FIG. 4 illustrates a stylized perspective view of an OCTASYSTEM implant installed in a root cavity between a pair of normal teeth. In particular, FIG. 4 illustrates a front view of a typical OCTASYSTEM implant and abutment 8, installed in the cavity left in the gingiva tissue 9 after the tooth and root have been extracted. Particular note should be taken of the fact that the abutment 8 by necessity, since it is screwed in place, is basically circular or cylindrical in form, and there is a gap between the abutment 8 and the gingival tissue 9 around the cavity 5. Thus the gingival tissue 9 is not held in place by the abutment 8. This leads to a serious gingival tissue shrinkage or collapse problem because after a few days, the unsupported gingival tissue 9 tends to shrink or collapse away from the adjacent teeth 11, and detract from the appearance of or create unsightly gaps in the gum line. In the prior art known to the inventor, no known technique or equipment is provided or taught, or even hinted at, for providing an abutment which is custom-shaped to fit within and support the walls of the gap or cavity left in the gingival tissue after tooth extraction and retain the gingival tissue in place so that the tissue retains an emergence healing profile similar to when the extracted tooth was in place.

Figure 5:
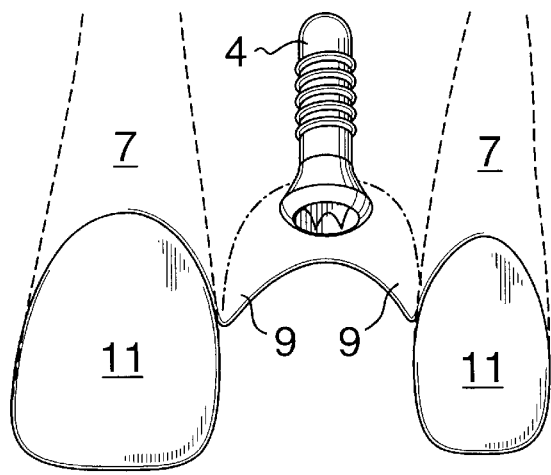
FIG. 5 illustrates a stylized perspective view of an OCTA-SYSTEM implant installed in a root cavity between a pair of normal teeth with roots.

FIG. 5 illustrates a stylized perspective view of an OCTASYSTEM implant installed in a root cavity between a pair of normal teeth with roots. As seen in FIG. 5, the octa-implant 4 is installed in the root cavity at the base of a tooth which has been extracted from the position between adjacent normal teeth 11 which are held in place by their respective roots 7. As seen in FIG. 5, the gingival tissue 9 has an attractive curved shape between the adjacent normal teeth 11, due to the fact that the tooth has been recently extracted. The base of the cavity is illustrated by dotted lines. However, over a period of several days, the gingival tissue 9, by not being supported, will shrink or collapse away from the adjacent normal teeth 11. The shrunk or collapsed gingival tissue creates unsightly gaps when the artificial tooth (not shown) is installed in the implant 4. Once the gingival tissue 9 has collapsed or shrunk away, it is virtually impossible to encourage the tissue 9 to expand into the gaps between the adjacent teeth. Surgery is required to restore the gum line.

Figure 6A:
FIG. 6a illustrates an enlarged perspective view of the octagonal tip of an OCTASYSTEM screwdriver.
Figure 6:
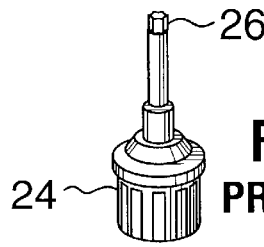
FIG. 6 illustrates a perspective view of an OCTASYSTEM screwdriver with octagonal tip.

FIG. 6 illustrates a perspective view of an OCTASYSTEM screwdriver 24 with octagonal tip 26. FIG. 6a illustrates an enlarged perspective view of the octagonal tip of an OCTASYSTEM screwdriver.

FIGS. 1 through 6a illustrate two existing Straumann and Friatec implant systems and emphasize in particular that there is no mechanism available to abut the gingival tissue surrounding the socket after tooth extraction. Implant systems supplied by other manufacturers also do not address this problem, or even recognize, perceive or acknowledge that tissue shrinkage is a problem.

The inventor has invented an emergence profile gingival tissue healing abutment system which ensures that gingival tissue surrounding the tooth extraction cavity is supported and cannot shrink after tooth extraction. This preserves the shape of the original gumline and enables attractive implant and crown systems to be installed. There are no unsightly tissue shrinkage gaps in the gumline after implant and crown installation.

Figure 7:
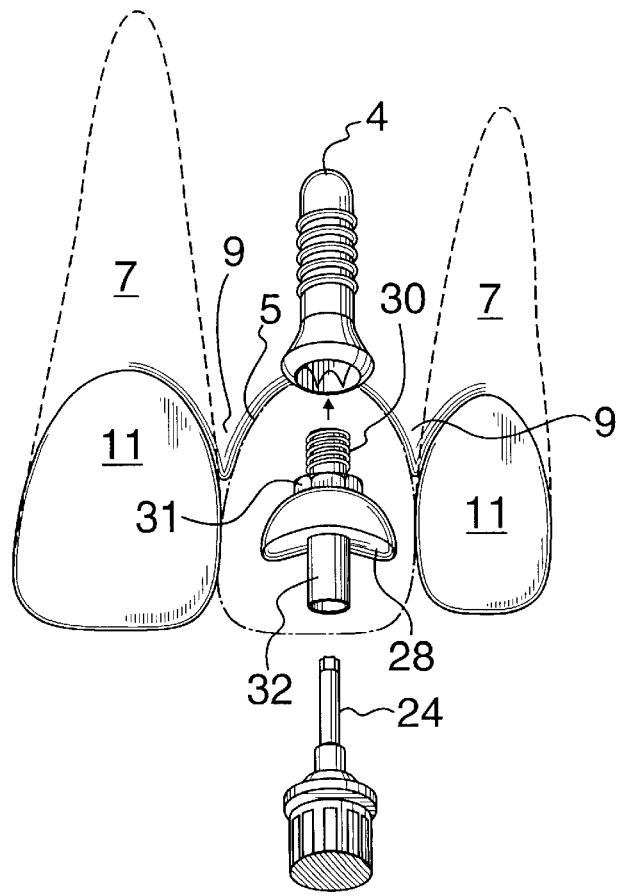
FIG. 7 illustrates a perspective view of a tissue emergence profile shaping healing abutment, screw and tube, according to the invention, ready for installation onto an Institut Straumann AG octa-implant, including a depiction of the screwdriver.

FIG. 7 illustrates a perspective view of a tissue emergence profile shaping healing abutment, screw and tube, according to one embodiment of the invention, adapted for installation onto an Institut Straumann OCTASYSTEM implant, including depictions of the OCTASYSTEM screwdriver. As seen in FIG. 7, a unique emergence profile healing abutment 28, with separate internal screw 30 (only the end of which is visible) octa-shaped base 31 and tube 32, according to the invention, is shown ready for installation by screwdriver 24 rotating screw 30 onto the threaded interior of the OCTASYSTEM implant 4, which was illustrated previously in association with FIG. 5. The internal screw 30, by being independent of the abutment 28, can be rotated by the implantologist into a tight position with the threads in the interior of the OCTASYSTEM implant 4 by screwdriver 24. The tissue emergence profile shaping healing abutment 28 is formed of a dentally acceptable resilient plastic, or some other dentally suitable material, which can be custom-shaped by the implantologist to fit in the specific concave gum cavity 5 which was illustrated in FIGS. 4 and 5 and thereby support the surrounding gingival tissue. Thus, because the abutment does not have to be rotated, but stays in one position, the implantologist can custom-shape the emergence profile healing abutment 28 so that it can be approximately oval or approximately triangular or approximately rectangular in horizontal cross-section shape to fit and fill the shape of the specific gum cavity 5 that pertains to the particular type and shape of tooth that has been extracted, such as a central incisor, a lateral incisor, a cuspid or a premolar (see FIG. 14), and support the adjacent tissue. It is important to note that, unlike the cylindrical implant systems in the prior art which rotate, the emergence profile healing abutment 28 according to the invention stays in the position in which it is installed by the implantologist and therefore is not and need not be cylindrical in shape. This is an important and unique breakthrough and enables an implantologist to ensure that the abutment 28, by being custom shaped, fits with and fills the specific gum cavity 5 so that the gingival tissue 9 surrounding the gum cavity 5 will be retained in position during the emergence profile healing process. In a sense, the emergence profile healing abutment 28, by being custom-fitted to fit and fill the tooth extraction cavity, and by remaining in that position because the octagonal base 31 holds it in position on the OCTASYSTEM implant 4, takes the place of the extracted tooth and holds the gingival tissue in its original position.

Figure 8:
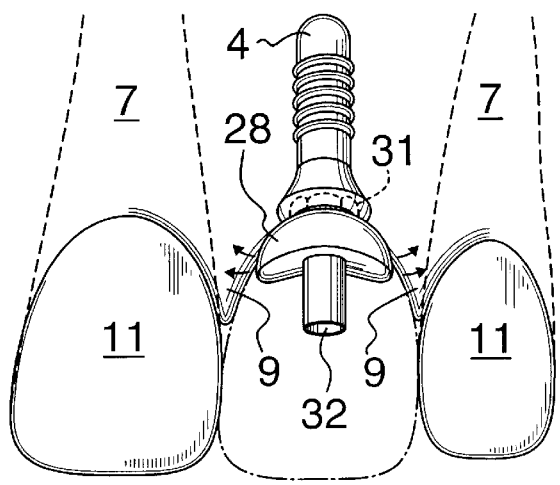
FIG. 8 illustrates a perspective view of the tissue emergence profile shaping healing abutment and tube installed onto the Institut Straumann AG OCTASYSTEM implant, and illustrates by means of directional arrows, how the emergence profile healing abutment retains the gingival tissue in position and prevents the gingival tissue from shrinking or collapsing due to non-support.
Figure 8:
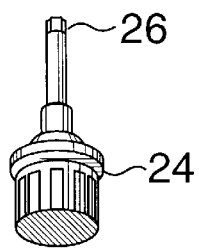

FIG. 8 illustrates an isometric view of the tissue emergence profile shaping healing abutment and tube installed onto the OCTASYSTEM implant 4, and illustrates by means of directional arrows, how the emergence profile healing abutment retains and supports the adjacent gingival tissue 9 in its original position and prevents the gingival tissue 9 from shrinking or collapsing due to non-support. The emergence profile healing abutment 28 is shown installed onto the Straumann OCTASYSTEM implant 4, with the tube 32 protruding from the emergence profile healing abutment 28. The hollow tube 32 can be square or rectangular in cross-section, or some other suitable cross-section, if required. The tube 32 can be cut away by the implantologist if required. The tissue supporting abutment 28, according to the invention, with its octagonal base 31, has been screwed in place in the octagonal interior of the Straumann OCTASYSTEM implant 4 by the screw 30 and the Straumann screwdriver 24 with the Octa-tip 26. For ease of illustration purposes, the octagonal base 31 is shown slightly separated (raised) from the octagonal recess of the OCTASYSTEM implant 4. In reality, the octagonal base 31 fits snugly within the octagonal recess and holds the abutment 28 in position. The same is true of FIGS. 9, 11 and 13. The outline of the eventual temporary crown is also shown in dotted lines in FIG. 8, in order to give the viewer a sense of what the finished tooth would look like.

Figure 9:
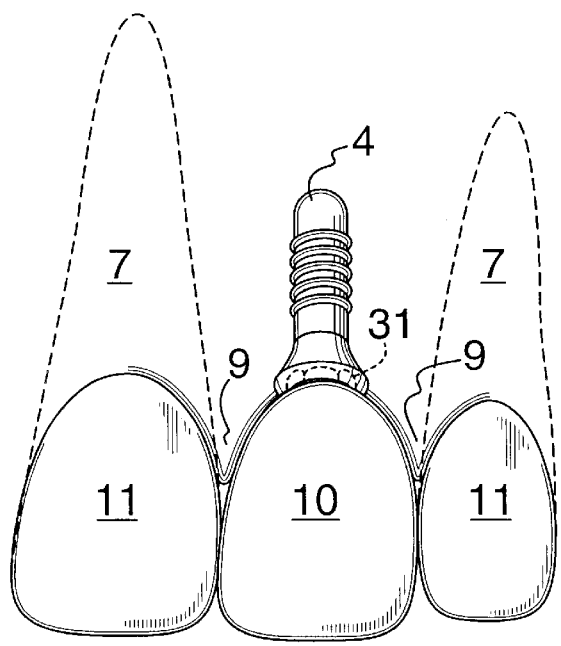
FIG. 9 illustrates a perspective view of an artificial tooth installed onto an OCTASYSTEM implant, between two normal teeth.
Figure 9:

FIG. 9 illustrates a perspective view of an artificial tooth (crown) 10 installed onto an OCTASYSTEM implant 4, between two normal rooted teeth 11. It will be noted that the adjacent gingival tissue 9 has remained in position and since no collapse or shrinkage has occurred, there are no unattractive gaps between the artificial tooth 10 and the original tooth 11. Shrinkage or collapse of tissue 9 would have occurred if the tissue 9 had not been supported by the tissue emergence profile shaping abutment 28 according to the invention during the healing process.

Related implant fittings and tools utilizing the inventor's unique basic tissue emergence profile shaping and healing abutment system manifest themselves into other embodiments and thus represent part of the overall invention.

FIG. 10 illustrates an exploded perspective view of a second embodiment of the invention comprising an emergence profile impression coping with OCTASYSTEM screw and plastic seating cap. An impression coping 34, together with a plastic seating cap 36 are shown in FIG. 10. The plastic seating cap 36 provides a positive seating of impression coping in the impression. The seating cap 36 as shown in FIG. 10 is cubical or cuboidal in shape. This configuration aids in helping the implantologist to align the coping 34, abutment 28. Other configurations of the screw housing tube or coping 34 are possible to suit specific requirements. The impression coping 34 registers and transfers the gingival emergence form accurately. The impression coping 34, abutment 28 is similar in concept and form to the tissue emergence profile healing abutment 28, tube 32 discussed previously and the provisional crown abutment discussed below in association with FIGS. 12 and 13.

FIG. 11 illustrates a perspective view of the emergence profile impression coping and plastic seating cap installed onto the OCTASYSTEM implant 4. As seen in FIG. 11, the impression coping 34 is installed in the octagonal cavity in implant 4 in position for the implantologist to take an impression. In this case, a cylindrical or disklike seating cap 36 is shown. As mentioned above, other suitable shapes of seating caps 36 are possible. Also, other suitable cross-section shapes of impression coping 34, including cylindrical or square, are possible, other than the one shown in FIGS. 10 and 11.

FIG. 12 illustrates an exploded perspective view of a third embodiment of the invention comprising an emergence profile provisional crown or final restoration abutment with screw 30 and plastic tube 32, used for providing a wax pattern for burnout according to conventional dental laboratory procedures. As seen in FIG. 12, the abutment 28, shaped by the implantologist to conform with the cavity in the gum left by the extracted tooth, is formed of plastic or some other dentally suitable material for wax pattern burnout in forming the final gold or ceramic crown, which will ultimately be installed on the OCTASYSTEM implant 4. The screw 30, for anti-rejection purposes, should preferably be formed of gold alloy or be gold plated. The tube 32 is formed of plastic as well. The tube 32, if desired, can be formed to be of another acceptable shape, such as square or rectangular cross-section.

FIG. 13 illustrates a perspective view of the emergence profile provisional crown or final restoration abutment, according to the invention, installed onto the OCTASYS- TEM implant 4 with a plastic tube used for wax pattern burnout. The tube 32 is removed. The shape of the artificial tooth, created in the dental laboratory, is illustrated in dotted line profile in FIG. 13.

Figure 14:
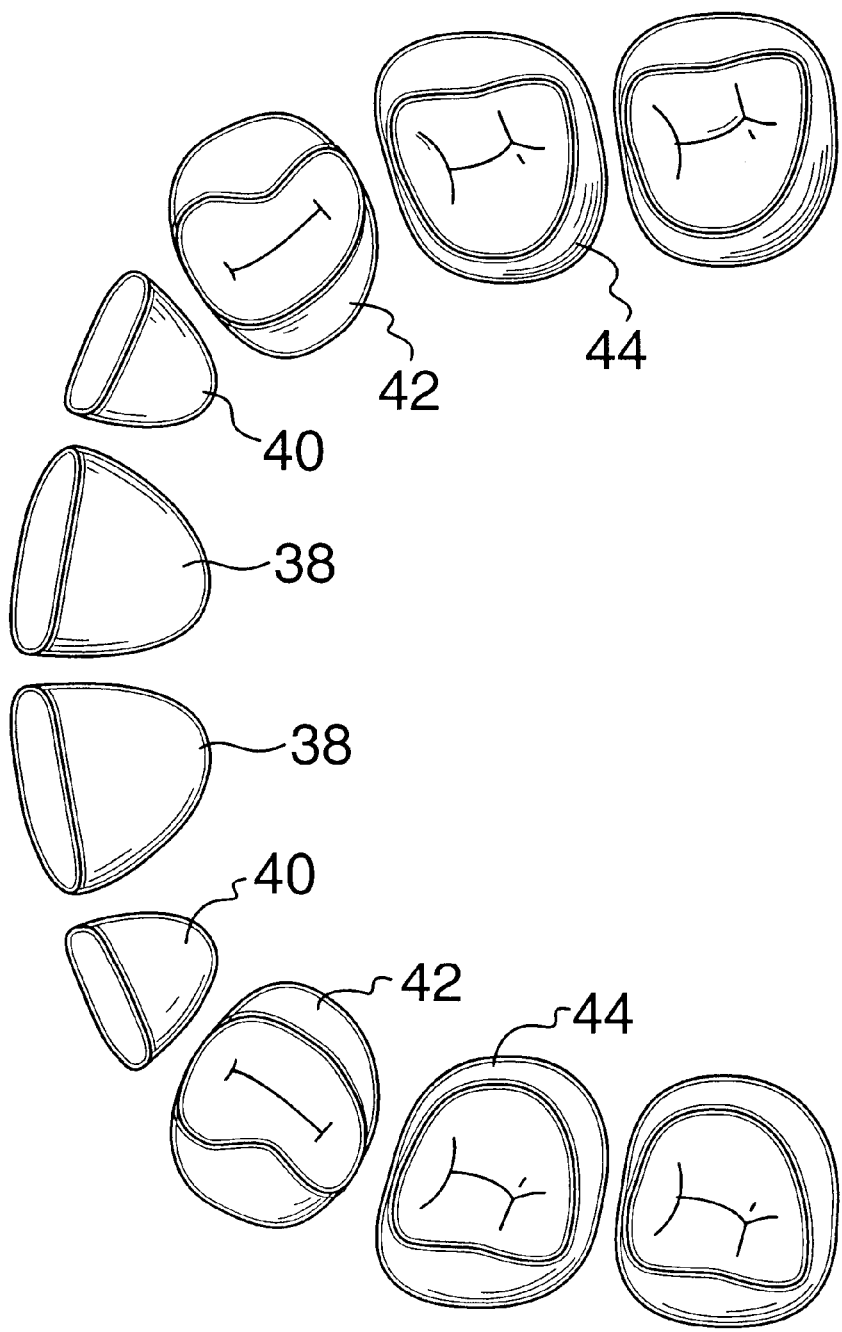
FIG. 14 illustrates a schematic view of the top front teeth of a human being including central incisors, lateral incisors, cuspids and premolars.

FIG. 14 illustrates a schematic view of the top front teeth of a human being including central incisors 38, lateral incisors 40, cuspids 42 and premolars 44. The emergence profile healing abutment 28 (as described previously) can be custom-shaped by the implantologist to accommodate any particular shape of gum cavity created by extracting a tooth. This is particularly important for the front teeth, which are more visible, and enable attractive shaping and retention of the gingival tissue, thereby preventing shrinking of the gingival tissue and creating unsightly gaps in the gum line along the visible adjacent teeth. As seen in FIG. 14, the abutment system according to the invention can be manufactured in four basic shapes and sizes to accommodate the approximately oval base of a typical central incisor 38, the approximately triangular base of a typical lateral incisor 40, the approximately square shape of a a typical cuspid 42 and the approximately rectangular shape of a typical premolar 44. While not shown in the drawings, the basic abutment 28 system according to the invention can be adapted to accommodate temporary crowns. It will be understood that while an octagonal base 31 is illustrated in the drawings, because it is compatible with the Straumann OCTASYSTEM, other base shapes such as hexagonal, which fit the Paragon or Friatec systems, or tapered, which fit the Moore taper of certain implant systems, are possible.

One important advantage of the emergence profile shaping healing abutment, impression coping, provisional and restoration abutments, wax pattern burnout and temporary crown base system according to the invention in its various embodiments is that it greatly reduces the number of components that must be manufactured for a typical dental implant system (see, for example, the large number of components that are illustrated in FIG. 2). Another important advantage, as discussed previously, is that the emergence profile healing abutment 28 according to the invention stays in one position when installed. It can thus be custom-shaped by the implantologist to abut, support and hold in position gingival tissue 9 which, if it were not abutted and supported, would shrink or collapse about the extraction cavity. A conventional implant abutment used in a commercially available implant system, by having to be circular or cylindrical in shape for screwing into the implant, does not abut and support the surrounding gingival tissue 9. As a result, the tissue shrinks or collapses and once this occurs, cannot be restored without surgery. Unattractive gaps in the gum line are the result.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A gingival tissue emergence profile shaping healing dental abutment for use in association with the installation of a dental implant in the jawbone of a patient comprising:
   (a) a provisional non-cylindrical gingival tissue supporting abutment with an implant bearing surface on a first side thereof, the abutment being formed of a dentally acceptable machinable material, the outer surface of which can be shaped by an implantologist to fit within a cavity of gingival tissue formed by extraction of a tooth and installation of a dental implant and support healing and prevent collapse or shrinkage of gingival tissue surrounding the cavity after extraction of the tooth;
   (b) a passage through the abutment and the bearing surface for receiving a screw to enable the bearing surface of the abutment to be secured to the dental implant; and
   (c) a hollow protrusion surrounding the passage and located on a second side of the abutment.

2. An abutment as claimed in claim 1 wherein the protrusion is a hollow tube which is in axial alignment with the passage and the implant.

3. An abutment as claimed in claim 1 including a screw which fits within the passage and connects the abutment with the implant.

4. An abutment as claimed in claim 1 wherein the bearing surface has an octagonal base for use in association with an octagonal recess implant.

5. An abutment as claimed in claim 1 wherein the abutment has an ovoid shape.

6. An abutment as claimed in claim 1 wherein the abutment has a tapered conical oval cross-section shape.

7. An abutment as claimed in claim 1 wherein the abutment has a tapered truncated shape with a triangular cross-section.

8. An abutment as claimed in claim 1 wherein the abutment has a tapered truncated shape with a rectangular cross-section.

9. An abutment as claimed in claim 1 including an impression coping and an associated seating cap.

10. An abutment as claimed in claim 9 wherein the seating cap is cylindrical or cuboidal in shape.

11. An abutment as claimed in claim 1 wherein the protrusion is a plastic tube which can be used for wax pattern burnout in forming a crown.

12. An abutment as claimed in claim 1 including a temporary crown associated with the abutment.

13. An abutment as claimed in claim 1 including a permanent crown associated with the abutment.

14. An abutment as claimed in claim 1 including a base for a ceramic crown restoration.

15. An abutment as claimed in claim 1 wherein the hollow protrusion is removed.

* * * * *

UNITED STATES PATENT AND TRADEMARK OFFICE
CERTIFICATE OF CORRECTION

PATENT NO.    : 6,386,876 B1
DATED         : May 14, 2002
INVENTOR(S)   : Lee, Dr. Kenneth K.S.

It is certified that error appears in the above-identified patent and that said Letters Patent is hereby corrected as shown below:

Column 4,
Line 10, delete "and abutment 8".
Lines 13, 15 and 17, delete "abutment" and insert -- implant --.

Column 6,
Line 32, before "coping", insert -- one-piece --.

Signed and Sealed this

Thirtieth Day of December, 2003

JAMES E. ROGAN
*Director of the United States Patent and Trademark Office*